United States Patent
Poplaw (10) Patent No.: US 9,474,489 B2
(45) Date of Patent: *Oct. 25, 2016

(54) PORTABLE SMART STETHOSCOPE FORMED OF SMART MOBILE DEVICE AND CASING ASSEMBLY

(71) Applicant: Barry Poplaw, North Miami, FL (US)

(72) Inventor: Barry Poplaw, North Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/719,340

(22) Filed: May 22, 2015

(65) Prior Publication Data

US 2015/0327812 A1 Nov. 19, 2015

Related U.S. Application Data

(63) Continuation of application No. 14/103,831, filed on Dec. 11, 2013, now Pat. No. 9,042,568.

(51) Int. Cl.

| | | |
|---|---|---|
| A61B 7/04 | (2006.01) | |
| H04R 25/00 | (2006.01) | |
| H04R 1/02 | (2006.01) | |
| H04R 9/06 | (2006.01) | |
| A61B 5/00 | (2006.01) | |
| H04M 1/02 | (2006.01) | |

(52) U.S. Cl.
CPC ............ *A61B 5/6898* (2013.01); *A61B 5/72* (2013.01); *A61B 7/04* (2013.01); *H04M 1/026* (2013.01); *A61B 2562/02* (2013.01)

(58) Field of Classification Search
CPC .. A61B 7/04; A61B 7/02; A61B 2562/0204; A61B 5/02055; A61B 5/6898; A61B 5/72; A61B 2562/02; H04R 1/46; H04M 2250/12; H04M 1/05; H04M 1/026
USPC ......... 381/67, 334, 333, 91, 151; 455/556.1, 455/550.1, 3.06
See application file for complete search history.

(56) References Cited

U.S. PATENT DOCUMENTS

| | | | |
|---|---|---|---|
| 6,790,178 B1* | 9/2004 | Mault et al. ................. 600/300 |
| 2007/0058818 A1* | 3/2007 | Yoshimine ....................... 381/67 |
| 2008/0146276 A1* | 6/2008 | Lee ............................ 455/556.1 |
| 2008/0273709 A1* | 11/2008 | Thiagarajan et al. .......... 381/67 |
| 2009/0213264 A1* | 8/2009 | Kim ............................... 348/374 |
| 2011/0301439 A1* | 12/2011 | Albert et al. ................. 600/301 |
| 2012/0190303 A1* | 7/2012 | Wong ............................ 455/41.2 |
| 2014/0012149 A1* | 1/2014 | Trice ............................. 600/528 |
| 2015/0087926 A1* | 3/2015 | Raz ....................... A61B 5/0013 600/301 |
| 2015/0104027 A1* | 4/2015 | Mulumudi ................ H04R 1/46 381/67 |

OTHER PUBLICATIONS

User Manual of CMS-VESD (Multi-functional Visual Stethoscope).

* cited by examiner

*Primary Examiner* — Vivian Chin
*Assistant Examiner* — Douglas Suthers
(74) *Attorney, Agent, or Firm* — Jundong Ma (57) ABSTRACT

A smart portable stethoscope is formed of a smart mobile device and a casing assembly for the mobile device. The casing assembly comprises a casing member, a diaphragm holder member configured to securely and effectively retain a diaphragm, and a vibrator-transducer member. The casing member includes a diaphragm connector part configured to securely fasten the diaphragm holder member to the casing member. The vibrator-transducer member is configured to be securely fastened to diaphragm holder member or casing member in such a manner that its vibrator is disposed to interconnect with the diaphragm and effectively duplicate vibrations captured by the diaphragm so as to deliver medical-grade auscultation electronic signal based on the duplicated vibrations to the mobile device through an electronic transmission channel coupling an audio interface of the mobile device and a signal-transmitting component of the vibrator-transducer member.

20 Claims, 7 Drawing Sheets

PORTABLE SMART STETHOSCOPE FORMED OF SMART MOBILE DEVICE AND CASING ASSEMBLY

CROSS-REFERENCE TO RELATED APPLICATION

This application is a continuation application claiming priority under 35 U.S.C. §120 to U.S. Non-provisional patent application Ser. No. 14/103,831, filed on Dec. 11, 2013, which claims the benefit under 35 U.S.C. §119(e) to U.S. Provisional Patent Application No. 61/735,977, filed Dec. 11, 2012, the entire disclosures of both of said prior applications being hereby incorporated by reference.

BACKGROUND

1. Technical Field

The present disclosure generally relates to a portable stethoscope, and more particularly relates to a portable smart stethoscope formed of a smart mobile device and a casing assembly.

2. Description of the Related Art

Stethoscopes are widely used in many fields, including human and veterinary medicine. A stethoscope can be used to auscultate sounds from different areas of a human or animal body, most commonly from the heart and lung thereof. A stethoscope can also be used to listen to various other sounds, such as bowel sounds, fetal heart sounds, blood pressure sounds, and sounds made when blood flows through narrow blood vessels. With the advancement of technologies, there have been attempts to build a portable smart stethoscope from a smart mobile device (such as a smart phone) by leveraging the computing power and communication capabilities of the smart mobile device, since such a portable smart stethoscope gives great promises in real time doctor-patient clinical encounters, remote and virtual medicine.

As one example, there were attempts to create smart phone applications which receive sound signals directly captured by the microphone on a host smart phone, analyze the captured sound signals, and aims to provide features using the captured sound signals. Features provided by the smart phone applications may include, e.g., detecting and displaying the heart rate and heart rhythm of a person, with the microphone of the host mobile device placed at or near the person's heart location. To Applicant's knowledge, a stethoscope formed with this line of approach simply cannot deliver "medical-grade" sound signals to a mobile device, and thus is not able to provide effective applications for serious medical uses.

As another example, there were attempts of using a separate electronic auscultation device in conjunction with a smart phone to form a smart stethoscope. More specifically, the separate electronic auscultation device collects auscultation data (e.g., from a human or an animal) and transmits the collected auscultation data to the smart phone either wirelessly via an antenna or using a wired headset plug through a microphone jack of the smart phone. The smart phone provides one or more auscultation related applications which use the wirelessly received auscultation data to provide various diagnosis features. Stethoscope formed with this line of approach requires a complete separate auscultation device from a smart phone, thus resulting in inconvenience in carriage, use, and storage.

Thus, there is a need for a portable smart stethoscope that not only can collect medical-grade auscultation data and leverage the computing power of a smart phone but also provide convenience in carriage, use, and storage.

BRIEF SUMMARY

In the first aspect, the present disclosure provides a smart stethoscope formed of a combination of a smart mobile device and a casing assembly adaptive to collect medical-grade auscultation data and provide collected auscultation data to the smart mobile device, thereby leveraging the computing power and communication capabilities of the smart mobile device to receive medical-grade auscultation data, and analyze and process the collected auscultation data in providing smart auscultation related applications.

In the second aspect, the present disclosure provides a casing assembly adaptive to be functioned not only as a compact and protective housing for a smart mobile device and but also as an auscultation device capable of collecting medical-grade auscultation data from the combination of a diaphragm securely retained in a diaphragm holder member of the casing assembly and a vibrator-transducer member tightly interconnected to the diaphragm within the casing assembly, and providing collected medical-grade data to the smart mobile device.

In the third aspect, the present disclosure provides a method of compactly fitting auscultation related components, along with the smart mobile device, into a housing formed by a casing, in such a manner the smart mobile device, auscultation related components, and the casing form an integral compact portable smart stethoscope.

In the fourth aspect, the disclosed casing assembly comprises a casing member including a diaphragm connector part, a diaphragm holder member configured to securely and effectively retain a diaphragm, and a vibrator-transducer member configured to effectively duplicate vibrations captured by the diaphragm, with the diaphragm connector part configured to securely fasten the diaphragm holder member to the casing member so as to form an integral assembly.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein.

DETAILED DESCRIPTION

In the following detailed description of exemplary embodiments of the disclosure, specific exemplary embodiments in which the disclosure may be practiced are described in sufficient detail to enable those skilled in the art to practice the disclosed embodiments. For example, specific details such as specific method orders, structures, elements, and connections have been presented herein. However, it is to be understood that the specific details presented need not be utilized to practice embodiments of the present disclosure. The following detailed description is, therefore, not to be taken in a limiting sense, and the scope of the present disclosure is defined by the appended claims and equivalents thereof. Also, descriptions of well-known functions and constructions are omitted for clarity and conciseness.

References within the specification to "one embodiment," "an embodiment," "embodiments", or "one or more embodiments" are intended to indicate that a particular feature, structure, or characteristic described in connection with the embodiment is included in at least one embodiment of the present disclosure. The appearance of such phrases in various places within the specification are not necessarily all referring to the same embodiment, nor are separate or alternative embodiments mutually exclusive of other embodiments. Further, various features are described which may be exhibited by some embodiments and not by others. Similarly, various requirements are described which may be requirements for some embodiments but not other embodiments.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. Moreover, the use of the terms first, second, etc. do not denote any order or importance, but rather the terms first, second, etc. are used to distinguish one element from another.

Within the descriptions of the different views of the figures, the use of the same reference numerals and/or symbols in different drawings indicates identical, similar, or close related items, and similar or closely related elements can be provided similar names, reference numerals, and reference alpha-numerals throughout the figures. If a reference numeral is once used to refer to a plurality of like elements, unless required otherwise by context, the reference numeral may refer to any, a subset of, or all of, the like elements in the figures bearing that reference numeral. Thus, for example, if reference numeral "338" is once referred to a fastening means or device or any element of the fastening means or device, reference numeral "338" may then also refer to any, a subset of, or all of, the elements of the fastening means or device, or the fastening means or device in its entirety, and reference alpha-numeral "338A" may then refer to one implementation or one portion of the fastening means or device, or any, a subset of, or all of the elements of that implementation or that portion. The specific identifiers/names, reference numerals and reference alpha-numerals assigned to the elements are provided solely to aid in the description and are not meant to imply any limitations (structural or functional or otherwise) on the described embodiments.

In the description, relative terms such as "left," "right," "vertical," "horizontal," "upper," "lower," "top" and "bottom" as well as any derivatives thereof (e.g., "left side," "upper sub winding," etc.) should be construed to refer to the logical orientation as then described or as shown in the drawing figure under discussion. These relative terms are for convenience of description and are not intended to convey any limitation with regard to a particular orientation.

Figure 1:
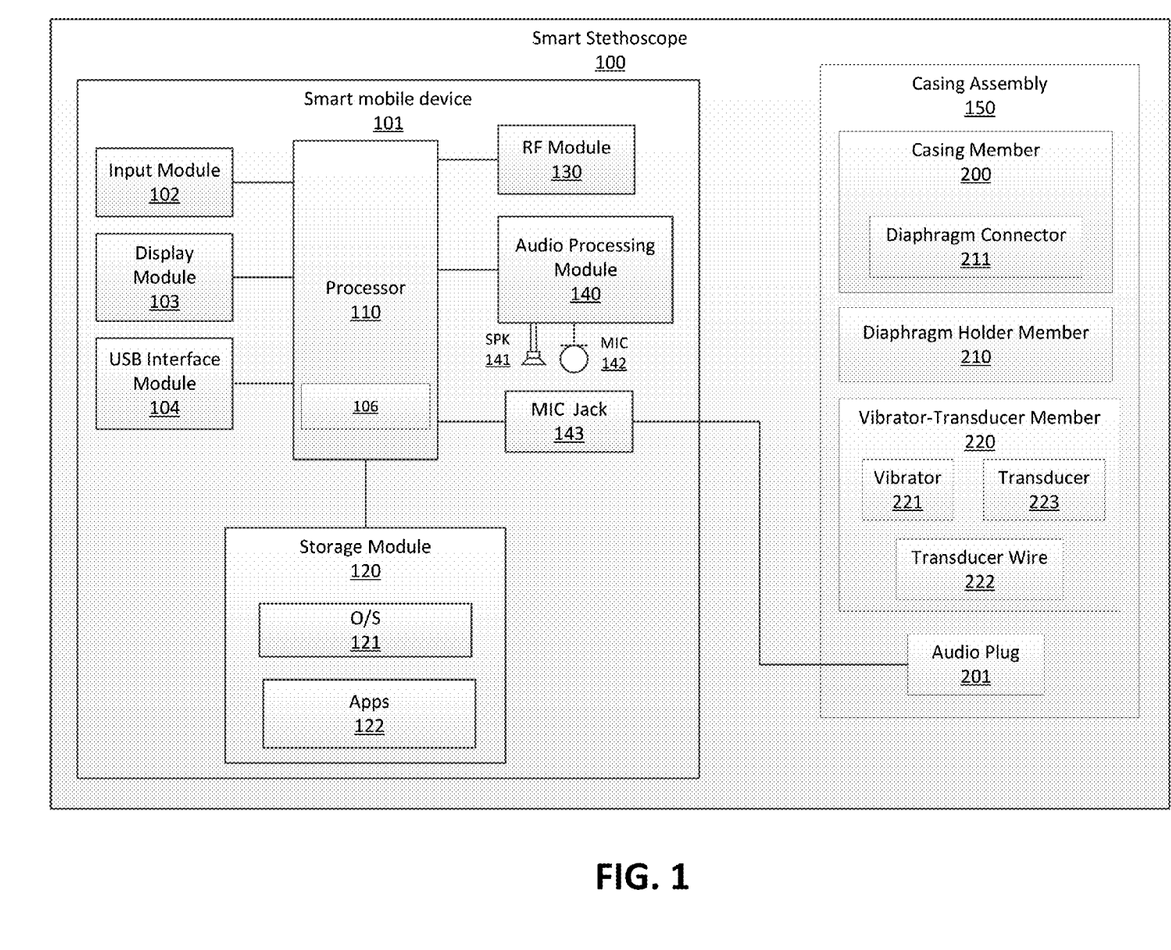
FIG. 1 is simplified functional block diagram illustrating a smart stethoscope 100 according to one or more embodiments of the present disclosure.

With reference now to the figures, and beginning with FIG. 1, there is illustrated a functional block diagram illustrating a smart stethoscope 100 according to one or more embodiments of the present disclosure. Referring to FIG. 1, smart stethoscope 100 comprises smart mobile device 101 (hereinafter simply referred to as "smart device") and casing assembly 150. Smart device 101 can be any smart portable device, such as a smart phone, a tablet PC, a laptop PC, a PDA, and etc. Smart device 101 comprises processor 110, which may be a microprocessor or a microcontroller.

Smart device 101 may further comprise an RF module 130, an input module 102, a display module 103, an audio processing module 140, a storage module 120, a microphone jack 143, and USB interface module 104, which are all communicatively coupled to processor 110 so as to either provide data to processor 110 or receive data from processor 110.

RF module 130 transmits and receives data wirelessly according to various communication protocols. Display module 103 can be any display device, such as an LCD display screen. Display module 103 may display user input information or output information provided by an application running on smart device 101. Display module 103 may include a touch screen which allows user to input data. In that case, display module 103 may serve as an input device.

Input module 102 receives input from a user and provides the received input to processor 110 for further processing by software programs running in processor 110. Input module 102 may include input keys, a touch screen, a QWERTY keyboard, a touchpad, or any combination thereof.

Storage module 120 stores application modules 122 and operating system modules 121, which may be loaded into processor 110 for execution. Storage module 120 may also store data used by application modules 122 and operating system 121. Storage module 120 may encompass any various internal and external storage media, such as RAM, ROM, smart card, flash memory, and any external storage medium accessible via wireless or wired communication means and/or one or more networks accessible to smart device 101.

USB interface module 104, which may include a USB or micro USB interface as well as USB switching circuit (not shown), allows the connection of an external device to smart device 101 via USB communication. With USB interface module 104, data from external device can be transmitted to processor 110 and may then be used by applications executed by processor 110 or transferred to another module, such as audio processing module 140, for further processing.

Microphone jack 143 allows connection of an external microphone to smart device 101 via a plug-and-jack connection so that audio signals captured by the external microphone (e.g. of an audio adaptor) can be transmitted to processor 110 (via the plug of audio adaptor) and may then be used by applications executed by processor 110 or transferred to another module, such as audio processing module 140, for further processing. Microphone jack 143 can be any jack that delivers audio signals to smart device 101. As one example, microphone jack 143 may be a dual microphone and audio jack which delivers audio signals from a microphone of an external headset to smart device 101 as well as delivers audio signals from smart device 101 to a headphone of the external headset.

Audio processing module 140 reproduces audio signals via speaker 141. Audio processing module 140 receives audio signals from microphone 142, converts audio signals into audible sound signals, and outputs audible sound signals via speaker 141. Audio processing module 140 may also receive audio data from processor 110, convert received audio data into audio sound signals, and output the sound signals via speaker 141.

In particular, audio data received from processor 110 may be provided from various sources, such as USB interface module 104, storage module 120, RF module 130, microphone jack 143, and audio data generated from one or more applications executed by processor 110. In one embodiment, processor 110 may include a switching control module 106, which detects audio signals from, e.g. USB interface module or microphone jack 143, and either supplies the audio signals to one or more applications executed by processor 110 or transfers the audio signals to audio processing module 140 for further processing.

Casing assembly 150 is adapted to not only compactly house smart device 101 for protection thereof but also collect medical-grade auscultation data. More specifically, casing assembly 150 may comprise casing member 200, diaphragm holder member 210, vibrator-transducer member 220, and audio plug 201.

Diaphragm holder member 210 is a an assembly or otherwise a structure configured to securely hold or otherwise dispose therein a diaphragm used to effectively capture surrounding or neighboring vibrations for medical purposes.

Casing member 200 may include a diaphragm connector part 211 configured to fasten or otherwise securely connect diaphragm hold member 210 to casing member 200 in such a manner that vibrations captured by the diaphragm (securely retained or otherwise securely disposed therein) are faithfully captured by vibrator-transducer member 220 disposed in casing assembly 150.

Vibrator-transducer member 220—which is configured to duplicate or otherwise capture vibrations captured by a neighboring interconnected diaphragm of medical-use, convert the captured vibrations into an electronic signal (analog or digital) representing the captured vibrations, and transmit the converted electronic signal—may include vibrator 221, transducer wire 222, and transducer 223. Vibrator 221 is configured to duplicate or otherwise capture vibrations captured by a neighboring interconnected diaphragm of medical-use by vibrating in accordance with vibrations captured by the neighboring diaphragm. Transducer 223, which is coupled to vibrator 221, is a known electronic device having integrated circuits (IC) configured to convert the vibrations captured by vibrator 221 to an electronic signal (analog or digital) representing the captured vibrations. Transducer wire 222, which is coupled to transducer 223, is configured to transmit the electronic signal generated by transducer 223 to an end device, such as audio plug 201, and usually comprises one or more signal lines collectively configured to carry and transmit the generated electronic signal.

Figure 2:
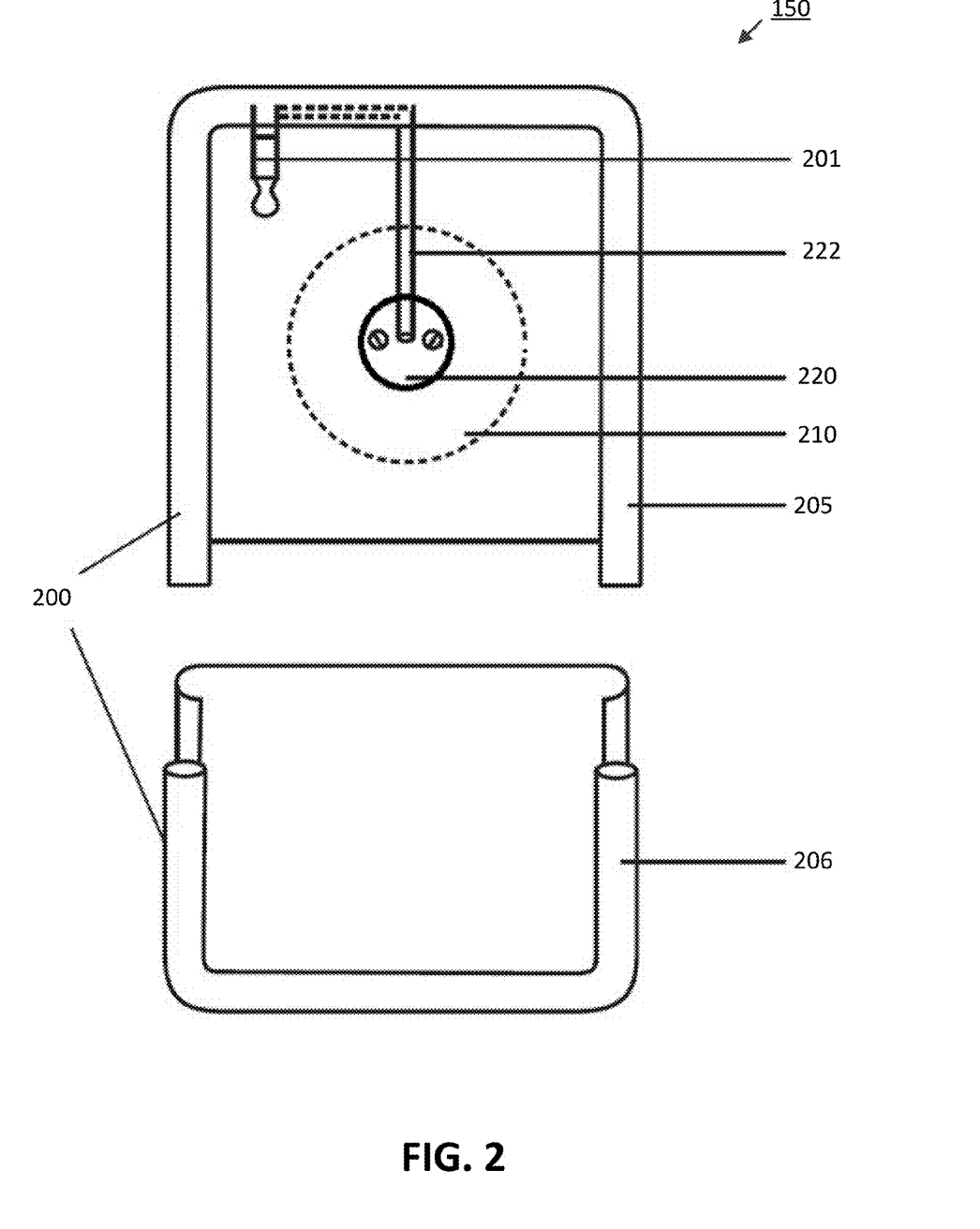
FIG. 2 is a perspective view illustrating casing assembly 150, particularly the front portion of casing member 200, according to one or more embodiments of the present disclosure.

FIG. 2 is a perspective view illustrating casing assembly 150, particularly the front portion of casing member 200, according to one or more embodiments of the present disclosure. As shown, casing member 200 is a casing adapted to compactly house a smart mobile device 101. In one exemplary implementation, casing member 200 comprises an upper body 205 and lower body 206. The receptacle on both vertical sides of upper body configured to mate the flange on both vertical sides of lower body such that when the flange of the lower body is fully pushed into the receptacle of the upper body, the upper body and lower body are securely fastened to each other to form a compact and protective housing for a smart mobile device 101. To fit a smart device 101 into the housing, the smart device may be slid into the partial housing formed by lower body 206 or the partial housing formed by upper body 205 before the upper body 206 and the lower body 205 mate with each other to form the complete housing.

As a skilled artisan appreciates, there can be myriad ways of making a casing member 200 purely for the purpose of housing and protecting a smart mobile device without departing from the scope and spirit of the present disclosure. For example, casing member 200 can be one integral piece without having an upper body and a lower body as shown.

As shown in FIG. 2, diaphragm holder member 210 is fastened to the back surface of upper body 205 (through diaphragm connector part 211). Vibrator-transducer member 220 is securely deployed or otherwise disposed within a close vicinity of diaphragm holder member 210 so as to effectively duplicate or otherwise capture vibrations captured by the diaphragm held in diaphragm holder member 210. Transducer wire 222 extends from vibrator-transducer member 220 to audio plug 201 positioned above an anticipated position of microphone jack 143 of a smart device 101 when the smart device 101 is properly housed within casing member 200.

Figure 3A:
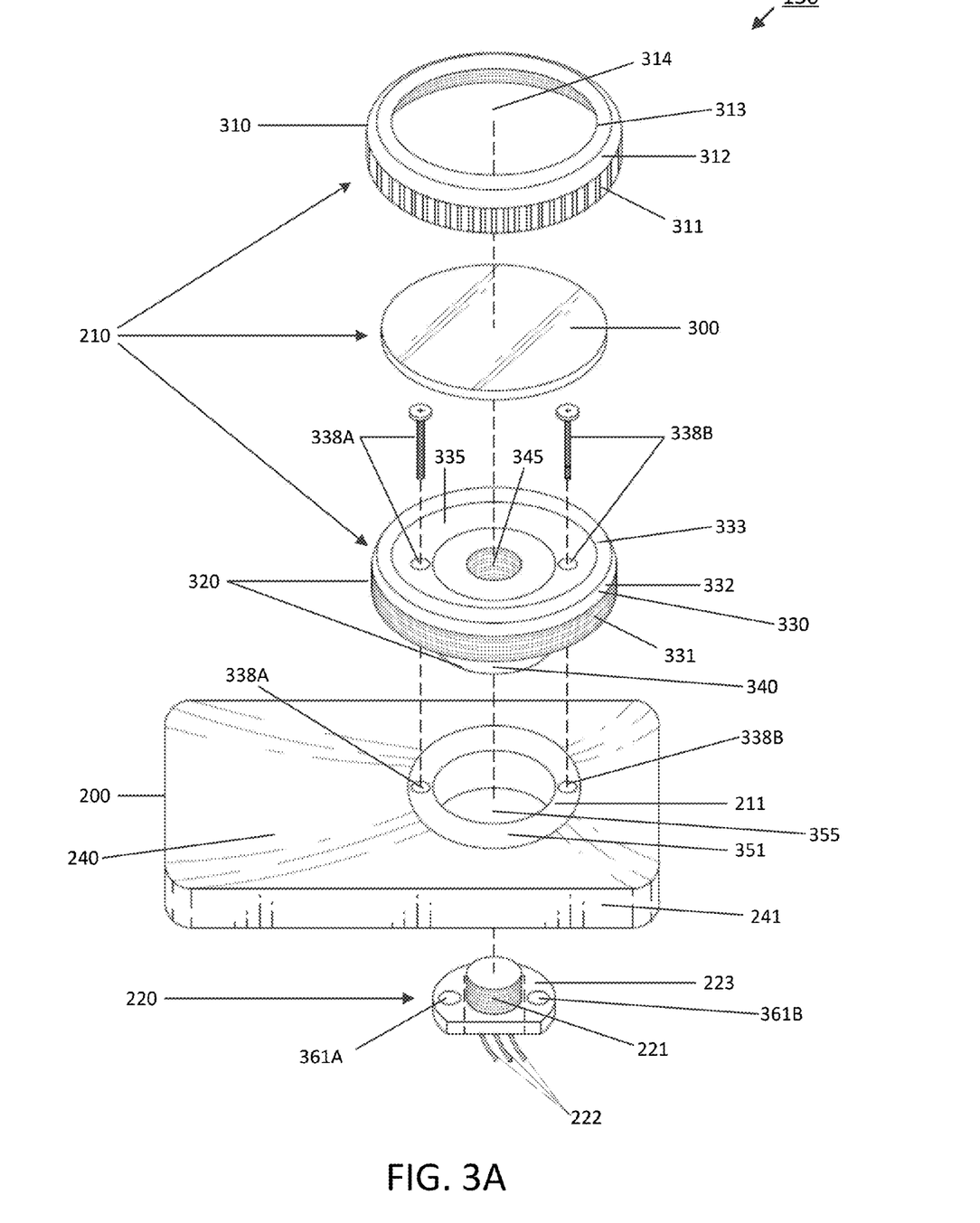
FIGS. 3A-E are exploded views and perspective views of an exemplary casing assembly 150 illustrating exemplary implementations of components including diaphragm holder member 210 and diaphragm connector part 211 of casing member 200, in accordance with one or more embodiments of the present disclosure.
Figure 3B:
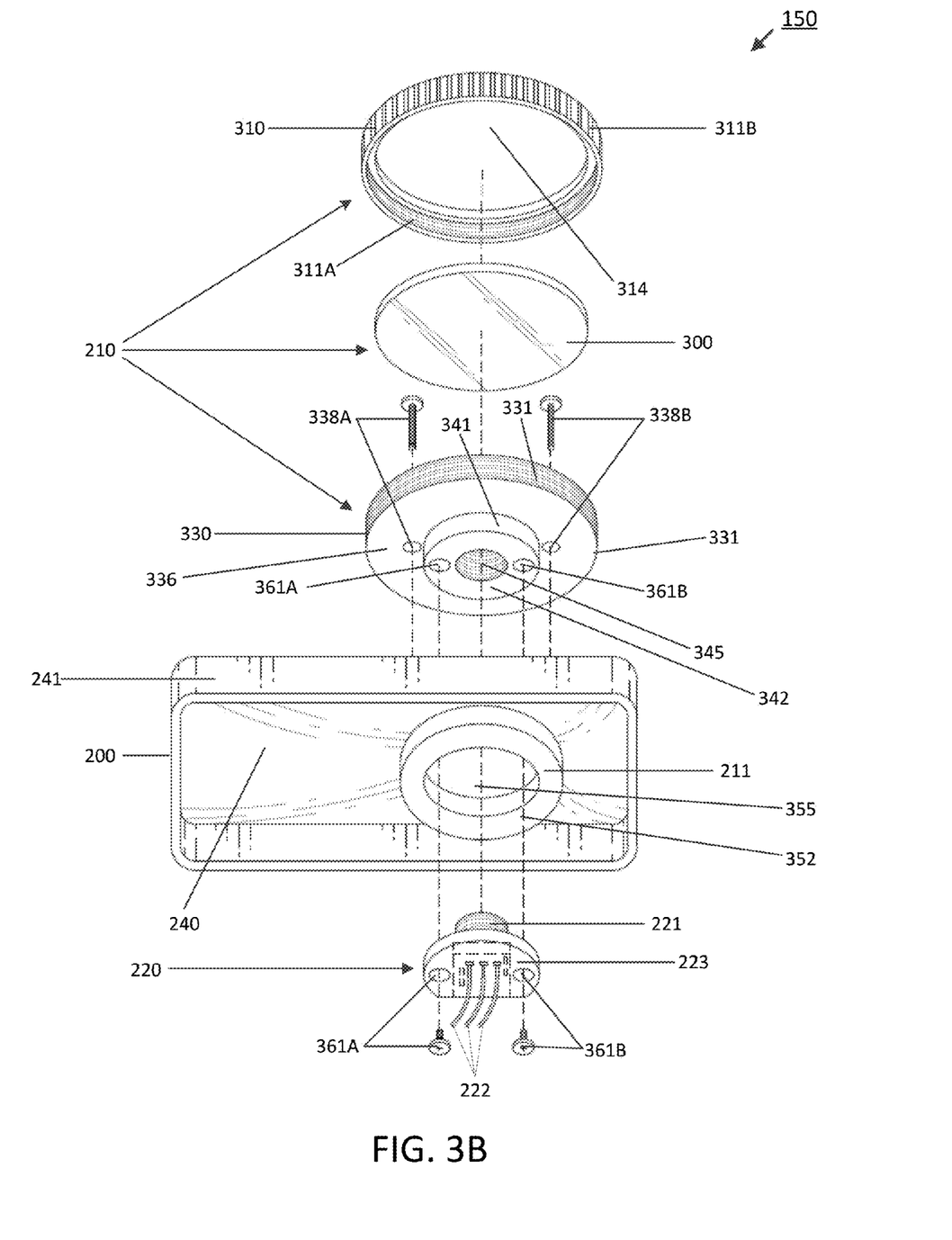

FIGS. 3A and 3B are both exploded views of an exemplary casing assembly 150 illustrating exemplary implementations of components including diaphragm holder member 210 and diaphragm connector part 211 of casing member 200. FIG. 3A uses top views of respective components of the exemplary casing assembly 150 for illustration while FIG. 3B uses bottom views of respective components of the exemplary casing assembly 150 for illustration.

Referring to FIGS. 3A and 3B, diaphragm holder member 210 may comprise, from upper to lower, a retention unit 310, a diaphragm 300, and a flange-shaft unit 320. Retention unit comprises, from lower to upper, a locking ring element 311, a transition element 312, and a rim element 313. Locking ring element 311, which is provided as the base of retention unit 310, is a ring-shaped structure having an inner surface with locking threads, thus serving as a coupling element for locking or otherwise tightly engaging the entire retention unit 310 to another object having an outer surface with complementary locking threads.

Transition element 312 is an angled annular structure extending between locking ring element 311 and rim element 313. The annular outer surface of transition element 312 is angled (tapered) upwards in extending from locking ring element 311 to overhang rim element 313, thus creating space 314 above ring element 311 and below rim element 313 while serving as another engaging surface in addition to the threaded inner surface of locking ring element 311. Rim element 313 is an annular rim extended from or affixed to the upper circumference of transition element 312, serving as an overhang to the aforementioned space 314 (created by transition element 312) for securing whatever (such as a diaphragm membrane) is placed thereunder.

Diaphragm 300 may be a slightly dome-shaped diaphragm membrane. As well-known, a diaphragm membrane can capture sound waves resulting from vibrations inside a human or animal body by converting sound waves into mechanical vibrations thereon, thus producing sound duplicative of internal sound of a human or animal body. The circumference of diaphragm 300 may substantially match the outer circumference of rim element 313 of retention unit 310. In one implementation, both the upper and lower circumferential edges of the diaphragm membrane may be sealed by a gasket to facilitate the interposing of the diaphragm membrane between two usually rigid annular surfaces, such as the lower surface of rim element 313. The annular width of the sealing gasket may substantially match the annular width of rim element 313.

Flange-shaft unit 320 is an integral structure comprising a flange part 330 and a tubular shaft 340. Flange part 330 comprises, from lower to upper, an anchor element 331, a transition element 332, and a rim element 333. Generally cylindrical-shaped anchor element 331 and tubular shaft 340 are concentrically and integrally joined to each other such that both upper surfaces thereof integrally form a unified annular upper surface 335 surrounding the cylindrical channel 345 of tubular shaft 340, with a tubular shaft portion 341 of tubular shaft 340 extending below the lower surface of anchor element 331.

The ring-shaped outer surface of anchor element 331 of flange part 330, which has a dimension substantially the same as the inner surface of locking ring element 311A of retention unit 310, has complementary locking threads to those of the inner surface of locking ring element 311. Both transition element 332 and rim element 333 of flange part 330, as in relation to the generally ring-shaped outer surface of anchor element 331, substantially match transition element 312 and rim element 313 of retention unit 310 as in relation to the locking ring element 311 of retention unit 310, in terms of structure and dimension, respectively.

With the generally matching configurations of retention unit 310 and flange part 330, retention unit 310 may tightly engage flange part 330 so as to tightly interpose and retain diaphragm 300 between their respective rim elements. Specifically, diaphragm 300 may be initially loosely interposed between retention unit 310 and flange part 330, as retention unit 310 is so disposed above flange part 330 as to have a lower portion of the threaded inner surface of locking ring element 311 of retention unit 310 slightly engage or press against an upper portion of the threaded outer surface of anchor element 331 of flange part 330. Then, a rotational force is continually applied to locking ring element 311 of retention unit 310 (particularly outer surface 311B of locking ring element 311) so that locking ring element 311 is driven downward to force anchor element 331 of flange part 330 to be increasingly received into ring element 311. The threads of the inner surface of locking ring element 31 increasingly engage the complementary threads of the outer surface of anchor element 331 as locking ring element 311 is rotationally driven downward, until the bottom of locking ring element 311 goes all the way downward to a level that is substantially in flush with the bottom of anchor element 331, at which point locking ring element 311 is in a full threaded locking engagement with anchor element 331.

The full threaded locking engagement between locking ring element 311 of retention unit 310 and anchor element 331 of flange part 330 also results in transition element 312 of retention unit 310 and transition element 332 of flange part 330 firmly pressing against and engaging each other, as well as rim element 312 of retention unit 310 and rim element 332 of flange part 330 tightly pressing against the upper and lower circumferential edges of diaphragm 300 from two opposing directions. Hence, the full threaded locking engagement between locking ring element 311 and anchor element 331 creates a locking engagement between retention unit 310 and flange part 330, which results in diaphragm 300 being securely retained between rim elements 313 and 333 while being able to freely vibrate in space 314 created by engaging transition elements 312 and 332. As such, threaded locking engagement between retention unit 310 and flange part 330 creates an integral assembly of diaphragm holder member 210 configured to securely retain (hold) diaphragm 300 while allow diaphragm 300 to effectively vibrate so as to effectively capture surrounding or neighboring vibrations of a targeted source of auscultation data (e.g., an internal organ of human or animal).

Anchor element 331 of flange part 330 additionally has a pair of fastening holes 338A and 338B each extended from its upper surface 335 all the way through its body to its lower surface 336, thereby forming a pair of fastening passages (holes) that can be used to fasten or otherwise securely connect the entire flange-shaft unit 320 to casing member 200.

Relatedly, as illustrated, casing member 200 has a back 240 whose body bulges from its peripherals areas towards a relatively flat upper annular surface 351 of diaphragm connector part 211, which is a tubular shaft 211 having a tubular housing (channel) 355 and integrally joined to back 240 via the upper annular surface 351. With the bulging configuration, tubular shaft 211 is afforded higher vertical depth (vertical length) than the vertical depth of a side 241 of casing member 200 which otherwise would be afforded to tubular shaft 211, in reference to the plane defined by the bottom edges of the four sides 241. The tubular housing (channel) 355 is of such a dimension (in terms of, e.g., diameter and depth) that it can snuggly receive the tubular shaft portion 341 of shaft 340 (which is extended below anchor element 331), such that the lower annular surface 342 of tubular shaft portion 341 is substantially in flush with the lower annular surface 352 of tubular shaft 211 as anchor element 331 of flange-shaft unit 320 rests on upper annular surface 351 of tubular shaft 211.

Upper annular surface 351 of tubular shaft 211 has two fastening holes 338A and 338B (which are drilled into the shaft body of tubular shaft 211) matching the two fastening holes 338A and 338B of anchor element 111 of flange-shaft unit 320, such that the two fastening holes 338A and 338B of annular surface 351 are respectively aligned with the two fastening holes 338A and 338B of anchor element 331 when anchor element 331 is aptly positioned and oriented on upper annular surface 351. These two pairs of vertical fastening holes 338A and 338B are used to fasten anchor element 311 to tubular shaft 211 so as to fasten flange-shaft unit 320 to casing member 200 using fastening screws, bolts, or other penetrating fastening devices. In one implementation, the shaft body of tubular shaft 211 is made of a durable material, and is of such a vertical depth that the two fastening holes 338A and 338B of tubular shaft 211 are both drilled into a vertical depth deep enough to secure the fastening of flange-shaft unit 330 to casing member 200 but without being drilled through the entire vertical depth of the shaft body of tubular shaft 211.

With the alignment of the vertical pair of fastening holes 338A and the alignment of the vertical pair of fastening holes 338B, a pair of screws, bolts, or other fastening devices 338A and 338B, may be inserted and screwed into (or otherwise driven into) the fastening holes 338A and 338B of annular surface 351 through the fastening holes 338A and 338B of anchor element 331, thereby fastening or otherwise securely connecting flange-shaft unit 320 to casing member 200 (via the body of its back 240) through fastening or otherwise securely connecting anchor element 331 to diaphragm connector part 211.

Figure 3C:
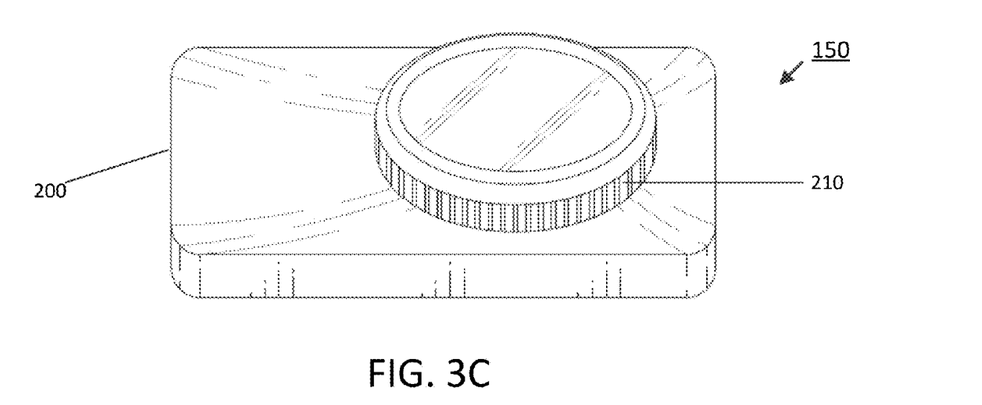

The fastening of flange-shaft unit 320 to casing member 200 may take place before the threaded locking engagement between retention unit 310 and flange part 330 of flange-shaft unit 320 take place to create an integral assembly of diaphragm holder member 210. As the assembly of diaphragm holder member 210 is created after the fastening of flange-shaft unit 320 to casing member 200, the diaphragm holder member 210 becomes fastened or otherwise securely connected to casing member 200 (via diaphragm connector part 211). FIG. 3C is a top view showing an integral assembly of diaphragm holder member 210 being securely fastened or otherwise securely connected to casing member 200.

Referring back to FIGS. 3A and 3B, as flange-shaft unit 320 is fastened to the body of back 240 of casing member 200, the tubular shaft portion 341 of shaft 340 is received into the tubular housing (channel) 355 of tubular shaft 211, with the lower annular surface 342 of tubular shaft portion 341 being substantially in flush with the lower annular surface 352 of tubular shaft 211. The body of tubular shaft portion 341 may be made of strong material, such as a metal. The lower annular surface 342 has two fastening holes 361A and 361B drilled into the body of tubular shaft portion 341.

Relatedly, vibrator-transducer member 220 is an integral assembly comprising a cylindrical-shaped vibrator 221 and a horizontally disposed plate-like transducer 223 having two fastening holes 361A and 361B matching the two fastening holes 361A and 361B of lower annular surface 342 of tubular shaft portion 341. The two vertical pairs of two fastening holes 361A and 361B are used to fasten the assembly of vibrator-transducer member 220 to tubular shaft portion 341 of the assembly of diaphragm holder member 210 with the use a pair of screws of 361A and 361B.

Cylindrical-shaped vibrator 221 is of such a dimension that vibrator 221 can be snuggly received into the tubular housing (channel) 345—which extends from the upper surface 335 to the lower annular surface 342—and vibrator 221 can have enough room above its top in the tubular channel 345 for vibrator 221 to vibrate unimpeded as needed within the tubular channel 345 when the assembly of vibrator-transducer member 220 is fastened to tubular shaft portion 341 of the assembly of diaphragm holder member 210 using fastening means 361.

Figure 3D:
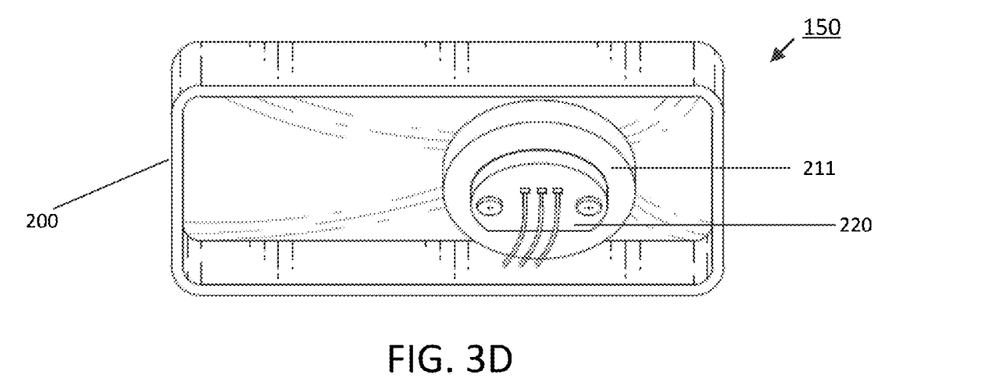
Figure 3E:
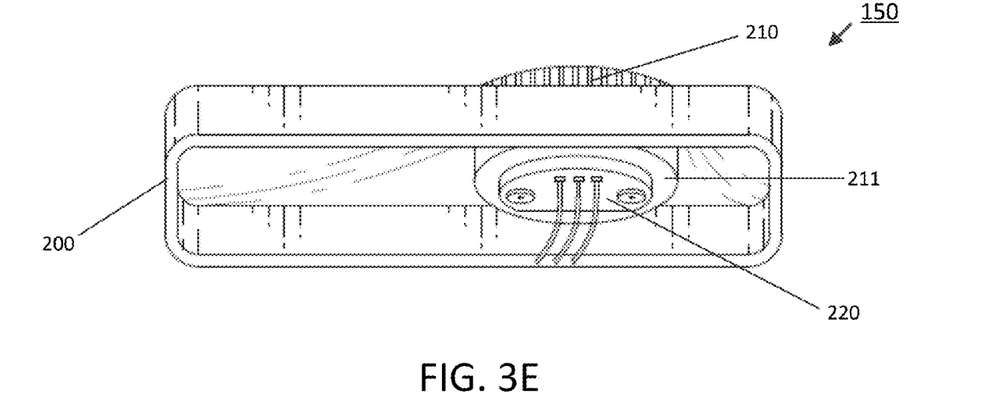

Thus, with fastening means 361 (which, in this example, includes fastening means 361A and 361B), the assembly of vibrator-transducer member 220 is fastened to the assembly of diaphragm holder member 210. FIG. 3D is a bottom perspective view illustrating the assembly of vibrator-transducer member 220 being fastened to tubular shaft portion 341 (not shown), which is disposed inside tubular channel 345 of tubular shaft portion 341 (of diaphragm holder member 210), which itself is disposed inside tubular channel 355 (of diaphragm connector part 211). As such, casing member 200, diaphragm holder member 210 and vibrator-transducer member 220 form an integral casing assembly 150. FIG. 3E is another perspective view illustrating the integral casing assembly 150 collectively formed by casing member 200, diaphragm holder member 210 and vibrator-transducer member 220 via diaphragm connector part 211.

As appreciated by a skilled artisan, with space 314 created by engaging transition members 312 and 332 below the securely retained diaphragm 300 and the interconnection between space 314 and the space in the tubular channel 345 above vibrator 221 disposed therein, diaphragm 300 and vibrator 221 are tightly, proximately, and effectively interconnected. This tight and proximate interconnection results in the freely vibratable vibrator 221 being capable of effectively and faithfully duplicating or otherwise capturing vibrations of the freely vibratable diaphragm 300, thus enabling transducer 223 to subsequently generate an electronic signal effectively and faithfully representing vibrations of diaphragm 300. As a skilled artisan readily appreciates, such an electronic signal is an auscultation signal of "medical-grade" quality unmatched by auscultation signals generated using the line of approach used by the first example described in the "Description of the Related Art" section.

In FIGS. 3A-3E, for illustration and not limitation, a fully assembled casing member 200 is provided to illustrate exemplary implementations of a casing assembly 150 including an integral assembly of a diaphragm holder member 210 integrally connected to casing member 200 via a diaphragm connector part 211 integrally joined to casing member 200. A skilled artisan appreciates that a part of a casing member 200, such as the upper body 205 illustrated in FIG. 2, may be similarly provided to form a casing assembly 150 including an integral assembly of a diaphragm holder member 210 integrally connected to the illustrated part of casing member 200 via a diaphragm connector part 211 integrally joined to the illustrated part of casing member 200.

Additionally, a skilled artisan appreciates that vibrator-transducer member 220 may be fastened to or otherwise securely connected to an integral assembly of a diaphragm holder member 210 using other schemes. For example, the plate-like transducer 223 may be fastened to lower annular surface 352 using fastening means similar to the illustrated fastening means 361.

Further, a skilled artisan appreciates that components illustrated in FIGS. 3A-3E may not be strictly drawn to scale. For example, relative to an actual casing member 200, diaphragm 300 as well as the formed integral assembly of diaphragm holder member 210, may, in some instances, be bigger or even substantially bigger than what they are illustrated in FIGS. 3A-E.

Figure 4:
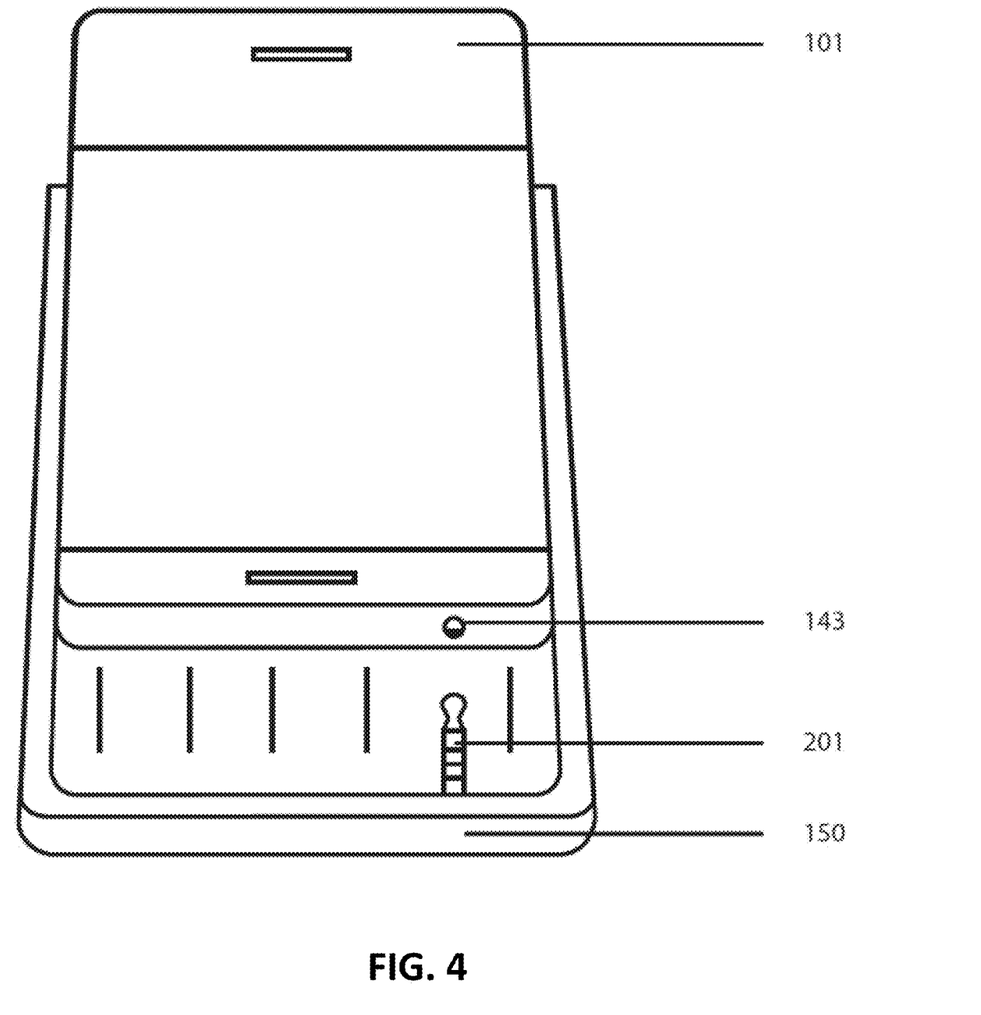
FIGS. 4 and 5 illustrate an example of how audio plug 201 can be plugged into microphone jack 143 so as to deliver medical-grade auscultation data in the context of casing assembly 150, in accordance with one or more embodiments of the present disclosure.
Figure 5:
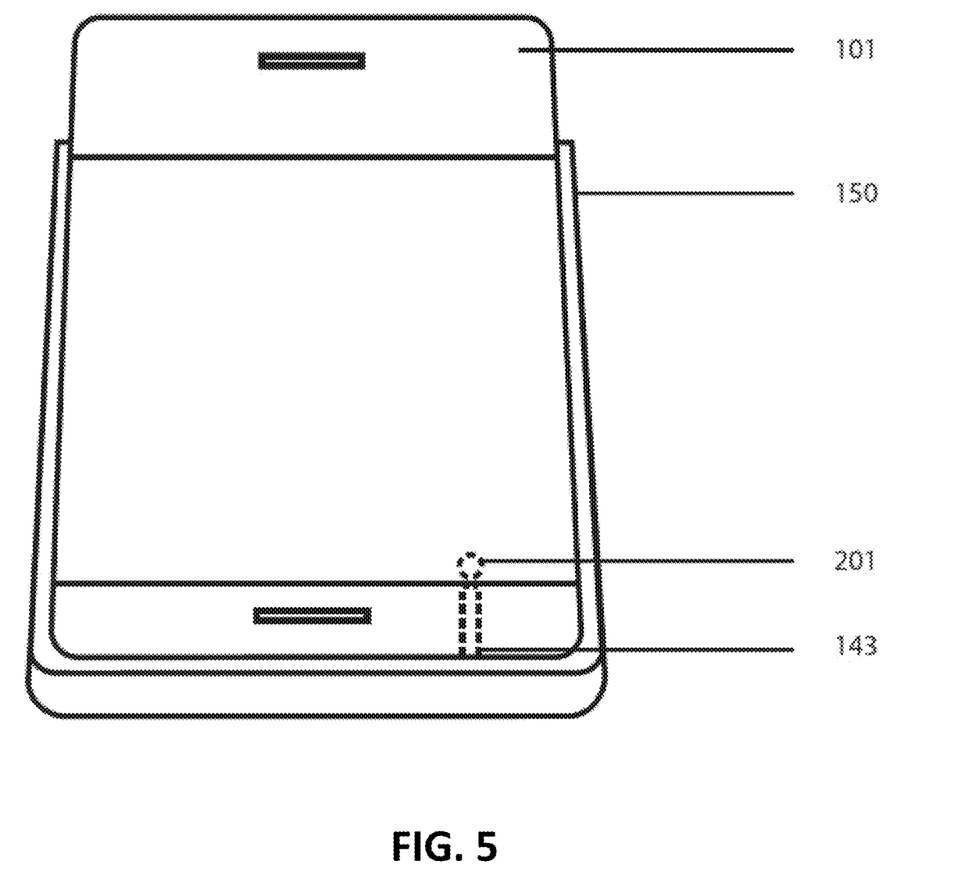

FIGS. 4 and 5 illustrate one embodiment where audio plug 201 is tightly situated within the housing (or partial housing) formed by casing member 200 (or upper body 205 of casing member 200) while being plugged into microphone jack 143, as the smart device 101 is being slid into the housing. As shown in FIG. 4, audio plug 201, with its spherical head facing towards microphone jack 143, is positioned at or near one horizontal side of the housing (the top side or the bottom side of the housing) in such a manner that its length is aligned with the anticipated line along which microphone jack 143 is lied. As shown in FIG. 5, when the smart device 101 is slid all the way into the housing (partial housing) such that one horizontal side of the smart device tightly fits against the aforementioned horizontal side of the housing, audio plug 201 is fully plugged into microphone jack 143, with its end receiving transducer wire 222 tightly situated against the aforementioned horizontal side of the housing.

In another embodiment, audio plug 201 may be plugged into microphone jack 143 from outside of casing member 200 via an aperture aligned with microphone jack 143 thereon such that microphone jack 143 is exposed to the outside through the aperture. Audio plug 201, on the other hand, may be extended to the outside of the back surface of casing member 200 through a passage configured to extend audio plug 201 and a portion of wire 222 to the outside without affecting the integral structure of casing assembly 150. In yet another embodiment, audio plug 201 is of USB interface, and thus is plugged into a USB or a micro USB interface connector in a manner similar to either of the two embodiments in connection with how audio plug 201 is plugged into microphone jack 143.

With the configurations illustrated in FIGS. 2-5, a smart portable device 101 and the integral casing assembly 150 form one integral portable smart stethoscope. Specifically, as well known, "medical-grade" auscultation sound can be collected by the securely retained diaphragm 300. Because of the tight configuration interconnection between diaphragm 300 and vibrator 221 of vibrator-transducer member 220, the collected "medical-grade" auscultation sound is captured by vibrator 221 and converted to analog or digital audio signals by transducer 223 of vibrator-transducer member 220. Thus, the converted audio signal is also a "medical-grade" replica of auscultation sound collected by diaphragm 300. The converted audio signal is transmitted from transducer 223 to the smart device 101 through a wired communication channel including transducer wire 222 of vibrator-transducer member 220, audio plug 201 and microphone jack 143 (or USB interface module 104). As noted above, microphone jack 143 (or USB interface module 104) is communicatively coupled to processor 110, which includes switching control module 106.

In one embodiment, switching control module 106 can detect audio signals transmitted from microphone jack 143 (or USB interface module 104) and transfer audio signals to one or more software applications installed in smart device 101 (which are usually referred to as "smart phone apps" or simply referred to as an "app") and executed by processor 110, or one or more modules such as audio processing module 140. The one or more executed software applications, upon receiving the transferred audio signals (which contain collected auscultation sound), may analyze, manipulate, store and/or transmit the collected auscultation sound data so as to provide various "smart" features in the areas of doctor-patient clinical encounters, remote and virtual medicine. Audio processing module 140, upon receiving the audio signals, may play the resulting auscultation sound in speaker 141, if desired. As such, an integral portable smart stethoscope, which delivers medical-grade auscultation sounds and various smart features related to auscultation, is therefore produced.

The advantages of the integral portable smart stethoscope are apparent. First, the smart mobile device 101 and casing assembly 150 form one integral smart stethoscope entity. This is in contrast to the second example discussed in the "Description of the Related Art" section where the auscultation device is completely separate from a smart mobile device. Thus, contrary to the combination used in the second example, the one integral smart stethoscope entity provides tremendous convenience to users in carriage, use and storage.

Second, the integral portable smart stethoscope delivers medical-grade sound and leverages the computing power and communication capabilities of a smart mobile device to provide various smart features. This is in direct contrast to the first example discussed in the "Description of the Related Art" section, where the use of a bare headset microphone simply cannot deliver medical-grade auscultation sounds, and as a result severely limits the usefulness of software applications which are forced to use low quality auscultation data. Thus, contrary to the first example, the disclosed portable smart stethoscope is able to deliver medical-grade auscultation sounds, and in turn allows applications to use medical-grade auscultation sounds, thereby greatly increasing the usability of a portable smart stethoscope.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof.

Therefore, it is intended that the disclosure not be limited to the particular embodiments disclosed for carrying out this disclosure, but that the disclosure will include all embodiments falling within the scope of the appended claims.

What is claimed is:

1. A smart portable stethoscope comprising:
   a smart mobile device of a portable size having:
      an audio interface configured to receive an electronic audio signal through an electronic transmission channel; and
      a processor configured to execute a software application programmed and configured to receive the electronic audio signal as an input through the audio interface via the electronic transmission channel; and
   a casing assembly housing the smart mobile device, said casing assembly having:
      a diaphragm holder member configured to securely retain a diaphragm in such a manner that enables the diaphragm to vibrate effectively to capture vibrations from a neighboring source of auscultation data;
      a casing member configured to form a housing adapted to house the smart mobile device, said casing member having:
         a back, the back configured to support one frame of the smart mobile device when the smart mobile device is received in the housing; and
         a diaphragm connector part attached to the back and configured to securely fasten to the diaphragm holder member in such a manner that the diaphragm holder member, the diaphragm connector part and the back form one tightly integrated physical structure within which the diaphragm holder member, the diaphragm connector part and the back are substantially non-movable with respect to one another; and
      a vibrator-transducer member having a vibrator, a transducer, and a signal-transmitting component, the vibrator-transducer member configured to be fastened to at least one of the diaphragm holder member and the casing member such that the vibrator is disposed to be interconnected with the diaphragm through one or more channels so as to effectively capture vibrations performed by the diaphragm, the transducer configured to convert the vibrator-captured vibrations to the electronic audio signal, the signal-transmitting component configured to be electronically coupled to the audio interface through the electronic transmission channel in such a manner that the electronic audio signal is delivered to the audio interface via the electronic transmission channel.

2. The smart portable stethoscope of claim 1, wherein the diaphragm holder member comprises a fastening means configured to securely fasten the diaphragm holder member to the diaphragm connector part of the casing member.

3. The smart portable stethoscope of claim 1, wherein the diaphragm holder member comprises diaphragm-retaining means having a first diaphragm-retaining part and a second diaphragm-retaining part, the first and second diaphragm-retaining parts are configured to form a locking engagement between each other, and the diaphragm-retaining means is configured to securely retain the diaphragm and create a diaphragm-vibrating space suitable for the retained diaphragm to vibrate effectively to capture a neighboring vibration when the first and second diaphragm-retaining parts are in the locking engagement between each other.

4. The smart portable stethoscope of claim 3, wherein the first diaphragm-retaining part comprises a first locking element, and the second diaphragm-retaining part comprises a second locking element; and wherein the first and second locking elements each have respective complimentary locking structures to form a locking engagement between each other in forming the locking engagement between the first and second diaphragm-retaining parts.

5. The smart portable stethoscope of claim 3, wherein the first diaphragm-retaining part comprises a first transition element and a first rim element, and the second diaphragm-retaining part comprises a second transition element and a second rim element; and wherein when the first and second diaphragm-retaining parts form the locking engagement between each other, the first and second transition elements are configured to have the diaphragm securely interposed there-between, and the first and second rim elements are configured to create the diaphragm-vibrating space suitable for the securely interposed diaphragm to vibrate effectively to capture neighboring vibrations.

6. The smart portable stethoscope of claim 3, wherein the diaphragm holder member further comprises a shaft part configured to form a first channel interconnected to the diaphragm-vibrating space and suitable for the vibrator of the vibrator-transducer member to vibrate effectively to capture the diaphragm-performed vibrations when the vibrator of the vibrator-transducer member is received inside the first channel.

7. The smart portable stethoscope of claim 3, wherein the diaphragm connector part of the casing member comprises a shaft sub-part configured to form a second channel interconnected to the diaphragm-vibrating space and suitable for the vibrator of the vibrator-transducer to vibrate effectively to capture the diaphragm-performed vibrations when the vibrator of the vibrator-transducer member is received inside the second channel.

8. The smart portable stethoscope of claim 1, wherein the audio interface comprises a wired electronic interface, the electronic transmission channel comprises a wired transmission channel, and the signal-transmitting component of the vibrator-transducer member comprises a set of electrical wires.

9. The smart portable stethoscope of claim 8, wherein the audio interface comprises a microphone jack, the electronic transmission channel comprises an audio plug, and the set of electrical wires of the signal-transmitting component of the vibrator-transducer member is electronically coupled to the microphone jack through the audio plug.

10. The smart portable stethoscope of claim 1, wherein said software application is programmed to use the received electronic audio signal to achieve at least one function for medical or clinical use.

11. A casing assembly for housing a smart mobile device of a portable size, the smart mobile device having an audio interface configured to receive an electronic audio signal through electronic transmission channel, the smart mobile device further having a processor configured to execute a software application programmed and configured to receive the electronic audio signal as an input through the audio interface, the casing assembly comprising:

a diaphragm holder member configured to securely retain a diaphragm in such a manner that enables the diaphragm to vibrate effectively to capture vibrations from a neighboring source of auscultation data;

a casing member configured to form a housing adapted to house the smart mobile device, said casing member having:

a back, the back configured to support one frame of the smart mobile device when the smart mobile device is received in the housing; and a diaphragm connector part attached to the back and configured to securely fasten to the diaphragm holder member in such a manner that the diaphragm holder member, the diaphragm connector part and the back form one tightly integrated physical structure within which the diaphragm holder member, the diaphragm connector part and the back are substantially non-movable with respect to one another; and a vibrator-transducer member having a vibrator, a transducer, and a signal-transmitting component, the vibrator-transducer member configured to be fastened to at least one of the diaphragm holder member and the casing member such that the vibrator is disposed to be interconnected with the diaphragm through one or more channels so as to effectively capture vibrations performed by the diaphragm, the transducer configured to convert the vibrator-captured vibrations to the electronic audio signal, the signal-transmitting component configured to be electronically coupled to the audio interface through the electronic transmission channel in such a manner that the electronic audio signal is delivered to the audio interface via the electronic transmission channel.

12. The casing assembly of claim 11, wherein the diaphragm holder member comprises a fastening means configured to securely fasten the diaphragm holder member to the diaphragm connector part of the casing member.

13. The casing assembly of claim 11, wherein the diaphragm holder member comprises diaphragm-retaining means having a first diaphragm-retaining part and a second diaphragm-retaining part, the first and second diaphragm-retaining parts are configured to form a locking engagement between each other, and the diaphragm-retaining means is configured to securely retain the diaphragm and create a diaphragm-vibrating space suitable for the retained diaphragm to vibrate effectively to capture neighboring vibrations when the first and second diaphragm-retaining parts are in the locking engagement between each other.

14. The casing assembly of claim 13, wherein the first diaphragm-retaining part comprises a first locking element, and the second diaphragm-retaining part comprises a second locking element; and wherein the first and second locking elements each have respective complimentary locking structures to form a locking engagement between each other in forming the locking engagement between the first and second diaphragm-retaining parts.

15. The casing assembly of claim 13, wherein the first diaphragm-retaining part comprises a first transition element and a first rim element, and the second diaphragm-retaining part comprises a second transition element and a second rim element; and wherein when the first and second diaphragm-retaining parts form the locking engagement between each other, the first and second transition elements are configured to have the diaphragm securely interposed there-between, and the first and second rim elements are configured to create the diaphragm-vibrating space suitable for the securely interposed diaphragm to vibrate effectively to capture a neighboring vibration.

16. The casing assembly of claim 13, wherein the diaphragm holder member further comprises a shaft part configured to form a first channel interconnected to the diaphragm-vibrating space and suitable for the vibrator of the vibrator-transducer to vibrate effectively to capture the diaphragm-performed vibrations when the vibrator of the vibrator-transducer member is received inside the first channel.

17. The casing assembly of claim 13, wherein the diaphragm connector part of the casing member comprises a shaft sub-part configured to form a second channel interconnected to the diaphragm-vibrating space and suitable for the vibrator of the vibrator-transducer to vibrate effectively to capture the diaphragm-performed vibrations when the vibrator of the vibrator-transducer member is received inside the second channel.

18. The casing assembly of claim 11, wherein the audio interface comprises a wired electronic interface, the electronic transmission channel comprises a wired transmission channel, and the signal-transmitting component of the vibrator-transducer member comprises a set of electrical wires.

19. The casing assembly of claim 18, wherein the audio interface comprises a microphone jack, the electronic transmission channel comprises an audio plug, and the set of electrical wires of the signal-transmitting component of the vibrator-transducer member is electronically coupled to the microphone jack through the audio plug.

20. The casing assembly of claim 11, wherein said software application is programmed to use the received electronic audio signal to achieve at least one function for medical or clinical use.

* * * * *